United States Patent
Logier et al.

(10) Patent No.: US 7,899,523 B2
(45) Date of Patent: Mar. 1, 2011

(54) FREQUENCY PROCESSING OF AN RR SERIES IN AN ANALOGUE CARDIAC SIGNAL

(75) Inventors: Régis Logier, Marcq-en-Baroeul (FR); Alain Dassonneville, Houplines (FR)

(73) Assignee: Centre Hospitalier Regional Universitaire de Lille, Lille Cedex (FR)

( * ) Notice: Subject to any disclaimer, the term of this patent is extended or adjusted under 35 U.S.C. 154(b) by 263 days.

(21) Appl. No.: 10/516,287

(22) PCT Filed: Apr. 16, 2003

(86) PCT No.: PCT/FR03/01226
§ 371 (c)(1),
(2), (4) Date: Feb. 21, 2006

(87) PCT Pub. No.: WO03/101291
PCT Pub. Date: Dec. 11, 2003

(65) Prior Publication Data
US 2006/0155199 A1 Jul. 13, 2006

(30) Foreign Application Priority Data
May 31, 2002 (FR) .................................... 02 06676

(51) Int. Cl.
*A61B 5/0468* (2006.01)
(52) U.S. Cl. .......... 600/516; 600/509; 600/511; 600/519
(58) Field of Classification Search ........... 600/508–528
See application file for complete search history.

(56) References Cited

U.S. PATENT DOCUMENTS

| | | | |
|---|---|---|---|
| 5,042,499 A | | 8/1991 | Frank et al. |
| 5,423,325 A | * | 6/1995 | Burton .......................... 600/515 |
| 5,560,370 A | * | 10/1996 | Verrier et al. ................. 600/518 |
| 5,596,993 A | * | 1/1997 | Oriol et al. ..................... 600/511 |
| 5,755,671 A | * | 5/1998 | Albrecht et al. .............. 600/516 |
| 5,842,997 A | * | 12/1998 | Verrier et al. ................. 600/518 |
| 6,216,032 B1 | * | 4/2001 | Griffin et al. ................. 600/515 |
| 6,330,469 B1 | | 12/2001 | Griffin et al. |
| 7,142,907 B2 | * | 11/2006 | Xue et al. ...................... 600/509 |

OTHER PUBLICATIONS

Bigger J T et al., "RR variability in healthy, middle-aged persons compared with patients with chronic coronary heart disease or recent acute myocardial infraction," Circulation, Apr. 1, 1995, pp. 1936-1943, vol. 91, No. 7, XP000610690, ISSN: 0009-7322, the whole document, American Heart Association, Dallas, TX.

* cited by examiner

*Primary Examiner* — Niketa I Patel
*Assistant Examiner* — Joseph Stoklosa
(74) *Attorney, Agent, or Firm* — Millen, White, Zelano & Branigan, P.C.

(57) ABSTRACT

The RR series, comprising a number of samples respectively defining the time interval between two successive heartbeats, is filtered by means of a digital band-pass filter ($F_k$), having a given band-pass [fc; f'c] and preferably by means of a recursive elective filter (RII). A variability index ($I_k$), is calculated which is a function of the instantaneous amplitude [vs(n)] of the discrete signal ($S_k$) coming from said band-pass filter. The variability index ($I_k$) is preferably a function of and particularly equal to the effective value of the discrete signal ($S_k$) from the band-pass filter.

12 Claims, 4 Drawing Sheets

FREQUENCY PROCESSING OF AN RR SERIES IN AN ANALOGUE CARDIAC SIGNAL

The present invention relates in general to the field of frequency analysis of an RR series made up from an analog bioelectrical signal, which series is characteristic of the cardiac rhythm of a living being, and is referred to herein as a "cardiac signal". Such frequency analysis is performed in order to extract automatically from the RR series one or more quantitative items of information serving to characterize the activity of the autonomous nervous system (ANS). The cardiac signal is preferably, but not exclusively, an electrocardiographic (ECG) signal, or a fetal cardiac signal measured by means of an electrode placed on the scalp of a fetus or by means of an ultrasound sensor placed on the mother's abdomen.

In this technical field, the invention mainly provides a method of frequency processing an RR series and a process for acquiring and electronically processing an analog cardiac signal using said frequency processing method. The invention also provides a system for acquiring and processing a cardiac signal in real time. A preferred, but non-exclusive, application of the invention lies in measuring and monitoring fetal suffering.

From a physiological point of view, the heart of a living being, when isolated from any external influence, contracts automatically in a manner that is very regular, like a metronome, thereby leading to spontaneous contraction of the cardiac muscle. Nevertheless, the heart is not isolated, but is connected to the autonomous nervous system (ANS) by the parasympathetic and the sympathetic systems. The autonomous nervous system influences the activity of the heart: the sympathetic system accelerates cardiac rhythm while the parasympathetic system slows it down. Thus, although it is autonomous to some extent, the heart is subjected to the influences of the autonomous nervous system, thus making it possible in particular for the organism of a living being to adapt heart rhythm as a function of needs, while nevertheless remaining within reasonable limits. Consequently, it will be understood that by analyzing changes over time in cardiac rhythm, and in particular by analyzing variations of cardiac rhythm (variation of heart beat), it is possible to obtain important information about the activity of the cardiac system, and more particularly about the activity of the autonomous nervous system. Knowledge about the activity of the ANS can be a precious aid in making a diagnosis in numerous clinical situations. On this topic, reference can be made for example to the following publication:

D. Lacroix, R. Logier, S. Kacet, J-R. Hazard, J. Dagano (1992): "Effects of consecutive administration of central and peripheral anticholinergic agents on respiratory sinus arrhythmia in normal subjects", J. of the Autonomic Nervous System, Vol. 29, pp. 211-218.

In order to study such fluctuations in cardiac rhythm, and thus the activity of the ANS, various techniques have been developed since 1970 for spectral analysis of a signal that represents changes over time in the instantaneous cardiac rhythm (or frequency), and that is obtained after sampling an analog bioelectrical signal, characteristic of the cardiac rhythm of a living being, and referred to below as the "cardiac signal".

Acquiring the Cardiac Signal and Constructing an RR Series

In order to acquire an (analog) cardiac signal, various invasive and non-invasive acquisition techniques are known. For example, a known invasive technique consists in using a blood pressure sensor connected to a catheter inserted in an artery. Amongst known non-invasive methods, there is to be found, for example, the use of an infrared pulse sensor, or the acquisition of an electrocardiographic (ECG) signal by means of an electrocardiograph. Also, in the field of fetal monitoring, it is known to use an appliance, commonly referred to as a "cardiotocograph" which serves to record simultaneously contractions of the uterus and heart beats of the fetus, which beats are picked up by an electrode placed on the scalp of the fetus or by an ultrasound sensor acting through the mother's abdominal wall.

Outside the particular field of fetal monitoring, the method of acquiring an ECG signal is the most widely used in practice at present, because not only is it non-invasive, but it also makes it possible advantageously to obtain a signal that is more precise than the signal obtained by means of an infrared pulse sensor, for example.

In known manner, an ECG signal is constituted by a succession of electrical depolarizations having the appearance as shown in accompanying FIG. 3. The P wave which corresponds to depolarization of the atria is of small amplitude and forms a dome. The PQ space represents the atrio-ventricular conduction time. The QRS complex reflects ventricular contraction, and the T-wave reflects ventricular repolarization. In practice, the R peak is considered as marking ventricular systole, i.e. the "heart beat".

In practice, since the R wave is usually the narrowest and largest-amplitude portion of the QRS complex, it is generally used for locating the heart beat instant to within very good precision, in practice of the order of one-thousandth of a second. Thus, the time interval between two successive R waves precisely characterizes the time between two successive heart beats; this is the period of the ECG signal and the reciprocal of this period is the instantaneous cardiac frequency.

For the purpose of automatically reconstructing the signal that represents changes over time in the instantaneous cardiac rhythm, which signal is referred to below as the "RR series", the analog ECG signal is sampled (analog-to-digital conversion of the ECG signal), and the sampled digital ECG signal is processed, with the R waves being detected automatically in the digital signal. In usual manner, an RR series is thus constituted by a plurality of successive samples (or points) ($RR_i$), with each sample ($RR_i$) corresponding to the time interval between two successive R waves of the ECG signal.

Nevertheless, it should be emphasized that it is also possible to use the other depolarization waves (P, Q, S, or T) in the ECG signal to characterize the cardiac frequency, even if measurement precision is then less good than when using R waves.

Furthermore, and depending on the acquisition technique that is selected, the cardiac signal may present a waveform that is different from the above-described waveform that comes from an ECG signal. Consequently, in the present specification, the term "RR series" is not limited to the particular definition given above on the basis of the R waves in an ECG signal, but is defined more generally in the context of the present invention as a series of a plurality of samples written $RR_i$, obtained after sampling an analog cardiac signal which is characteristic of cardiac rhythm, with each sample $RR_i$ being characteristic of the time interval between two successive heart beats. Thus, an RR series in the context of the invention can be constructed equally well from any known type of cardiac signal: an ECG signal, a cardiac signal measured by a blood pressure sensor or by an infrared pulse sensor, a fetal cardiac signal measured by an ultrasound sensor or by a scalp electrode, etc. . . . .

Spectral Analysis

Spectral analysis of an RR series from a cardiac signal is usually implemented in two main stages.

In a first stage, the curve for the spectral density of the RR series is computed, e.g. over the range 0 to 2 hertz (Hz), using various known methods. The method in most widespread use consists in computing the discrete fast Fourier transform of the RR series in predefined time windows that are weighted by means of a predefined weighting window. Depending on the intended implementation, it may be a rectangular weighting window, or, for example, it may be a Kaiser, Hamming, or Bartlett weighting window. Similarly, the computation time windows may be predefined and constant, or the computation time window may be of predetermined size but caused to slide over time. For example, the Fourier transform is computed over a sliding time window of 256 seconds (s) duration applied to the RR series and subjected to Kaiser weighting in order to limit the edge effects due to the windowing.

In a second stage, starting from the spectral density curve obtained at the end of the first stage, the spectral powers (the areas under the spectral density curve) are computed automatically between predetermined frequency bounds, that are optionally user adjustable.

Such spectral power computations enable quantitative information to be obtained characteristic of the activity of the autonomous nervous system (ANS), thereby constituting means for investigating and analyzing cardiac regulation by the ANS. For example, a low frequency spectral power (LF-SP) is computed over a frequency range of 0.039 Hz to 0.148 Hz, and a high frequency spectral power (HF-SP) is computed over a frequency range of 0.148 Hz to 0.4 Hz. In general, it is considered that for an adult, the low frequency spectral power (LF-SP) provides quantitative information characteristic of sympathetic and parasympathetic tone, while the high frequency spectral power (HF-SP) provides quantitative information characteristic of parasympathetic tone.

The above-described method of spectral analysis presents several drawbacks.

Computing the spectral density curve by the fast Fourier transform (or by equivalent means) is relatively expensive in terms of computation power and/or computation time, and at present that makes this method of spectral analysis unsuitable for implementation in a miniature portable system and/or difficult to implement in real time.

Likewise, in order to obtain acceptable frequency resolution, the fast Fourier transform needs to be computed over time windows that are relatively large (e.g. 256 s), which corresponds to a large number of samples of the RR series. As a result, this method of spectral analysis is accompanied by a "memory" effect which slows down the taking into account of any change that might occur in the cardiac signal.

Thus, a main object of the present invention is to propose a novel method of automatically processing an RR series, which method, in a manner comparable to the above-described method of spectral analysis, makes it possible to compute automatically at least one quantitative item of information (parameter) from the RR series that is characteristic of ANS activity, but mitigates the above-mentioned drawback.

This object is achieved by a novel method of frequency processing an RR series, which method comprises filtering the RR series by means of at least one digital bandpass filter ($F_k$) presenting a predefined bandwidth [fc, f'c], and computing a variability index ($I_k$) that is a function of the instantaneous amplitude [vs(n)] of the discrete signal ($S_k$) from said bandpass filter.

Compared with known methods of spectral analysis, the method of the invention presents the advantage of being simpler to implement and of requiring less computation time and/or power, while nevertheless being finer and providing better response time.

In a preferred variant implementation, the variability index ($I_k$) is a function of, and is preferably equal to, the root mean square (rms) value of the discrete signal ($S_k$) from the bandpass filter.

More precisely, in accordance with the invention, but in a manner that is not limiting on the invention, a digital filter is used of bandwidth lying in one of the following frequency bands:

[0.04 Hz, 0.15 Hz];
[0.15 Hz, 2 Hz] and preferably [0.15 Hz, 0.5 Hz];
[0.05 Hz, 0.07 Hz];
[0.04 Hz, 2 Hz] and preferably [0.04 Hz, 0.5 Hz];
[0.03 Hz, 0.15 Hz] and preferably [0.031 Hz, 0.102 Hz];
[0.1 Hz, 2 Hz] and preferably [0.102 Hz, 0.5 Hz].

In a particular variant of the invention, the RR series is filtered by means of a plurality of filters ($F_1, F_2, \ldots$), and a frequency variability index is computed that is a function of a plurality of variability indices ($I_1, I_2, \ldots$) that are computed in parallel.

More particularly, in a first variant implementation, the RR series is filtered by means of at least two filters ($F_1, F_2$) of bandwidth lying respectively in the following frequency bands:

$F_1$: [0.04 Hz, 0.15 Hz];
$F_2$: [0.15 Hz, 2 Hz] and preferably [0.15 Hz, 0.5 Hz];

and a frequency variability index is computed as a function of the variability indices $I_1$ and $I_2$.

In a second variant implementation, the RR series is filtered by means of at least two filters ($F_1, F_2$) of bandwidth lying respectively in the following frequency bands:

$F_1$: [0.03 Hz, 0.15 Hz] and preferably [0.031 Hz, 0.102 Hz];
$F_2$: [0.1 Hz, 2 Hz] and preferably [0.102 Hz, 0.5 Hz];

and a frequency variability index is computed as a function of the variability indices $I_1$ and $I_2$.

The invention also provides a process for acquiring and electronically processing an analog cardiac signal characteristic of cardiac rhythm. This process is known insofar as the cardiac signal is recorded, the signal is digitized, and an RR series is constructed.

In a manner characteristic of the invention, the RR series is processed automatically in real time as said series is being constructed, by implementing the above-specified frequency processing method of the invention.

Finally, the invention provides a system for acquiring and processing a cardiac signal in real time, which system comprises acquisition means enabling a cardiac signal to be acquired, first electronic means enabling an RR series to be constructed automatically, the series being constituted by a plurality of samples ($RR_i$) defining respective time intervals between two successive heart beats.

In a manner characteristic of the invention, the acquisition and processing system further comprises second electronic means for processing the RR series delivered by the first electronic means in accordance with the frequency processing method of the invention.

In a preferred use of the invention, the acquisition and processing system constitutes a cardiotocograph including a novel function of measuring fetal suffering.

Other characteristics and advantages of the invention appear more clearly on reading the following description of two preferred variant implementations, which description is made with reference to the accompanying drawings:

BRIEF DESCRIPTION OF DRAWINGS

FIG. 1 shows a system for acquiring and frequency processing cardiac rhythm. The system comprises:
  conventional means for acquiring an ECG signal, comprising a plurality of measurement electrodes 1 connected to inputs of an electrocardiograph monitor 2; and
  means 3 for real time processing of the ECG signal output by the ECG monitor 2.

The processor means 3 for processing the ECG signal comprise an analog-to-digital converter 4 and a programmed processor unit 5. The input of the converter 4 is connected to the output of the ECG monitor 2, and the output of the converter 4 is connected to an input port of the processor unit 5. In a particular implementation that is not limiting on the invention, the processor unit 5 is constituted by a microcomputer, and the converter 4 is connected to an RS232 serial port of the microcomputer.

Figure 3:
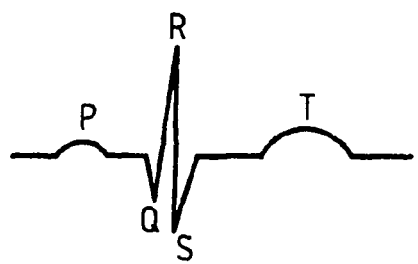
FIG. 3 shows the PQRST wave characteristic of an analog ECG signal.

In operation, the electrodes 1 are applied to the body of a patient, and the ECG monitor outputs in conventional manner an analog electrical signal referred to as the ECG signal, which, for each heart beat, has a signal waveform as shown in FIG. 3. The ECG signal is digitized by the converter 4 as a predetermined sampling frequency (f), e.g. a frequency of 256 Hz. The digital signal (shown in FIG. 4) is then processed in real time by the processor unit 5, using specific processing software described in detail below.

Analog ECG Signal—FIG. 3

The electrocardiographic signal (ECG) output by the ECG monitor 2 is constituted by a set of electric waves having the appearance given in FIG. 3.

The P wave which corresponds to depolarization of the atria is of small amplitude and is dome-shaped; the PQ space represents the atrio-ventricular conduction time; the QRS complex reflects ventricular contraction; and the T wave reflects ventricular repolarization. In practice, it is considered that the R wave is a marker of ventricular systole, or of "heart beat".

Figure 4:
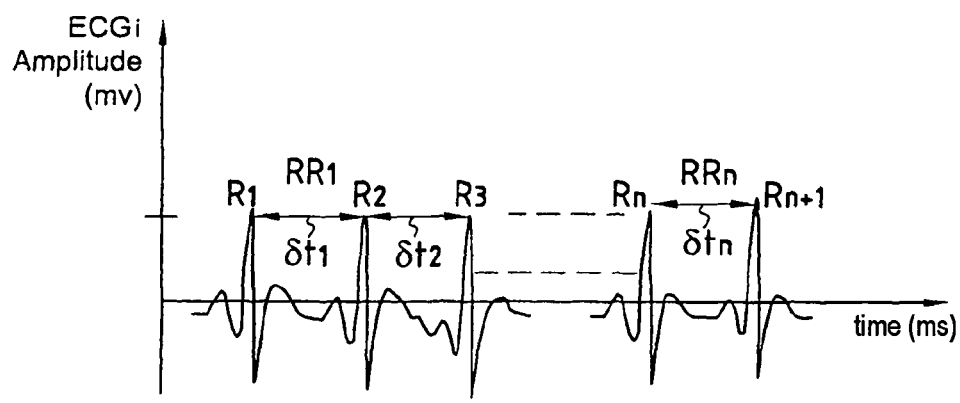
FIG. 4 shows an example of the digital $ECG_i$ signal as obtained after sampling an analog ECG signal.
Figure 5:
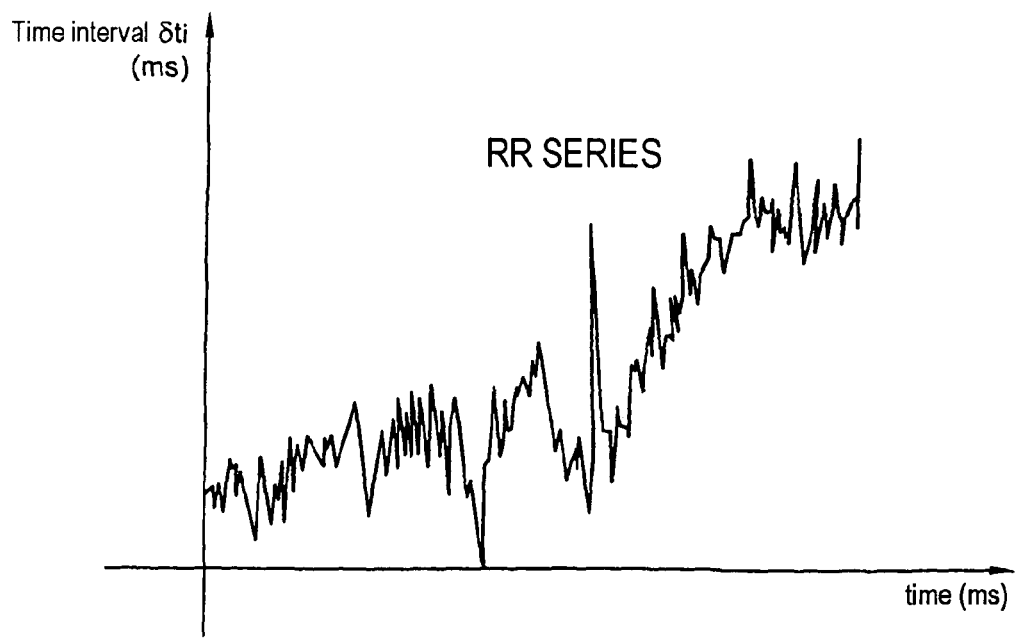
FIG. 5 shows the RR series constructed from the signal of FIG. 4.

The RR Interval—FIG. 4

The "RR" interval corresponds to the time between two heart beats, and is the instantaneous period of the signal, so its reciprocal gives the instantaneous cardiac frequency. Since the R wave is usually the finest and largest-amplitude portion of the QRS complex, it serves to provide a point location for the heart beat with very good precision (of the order of one-thousandth of a second).

Recording the succession of R waves on the basis of the ECG signal enables the RR series to be constructed and enables it to be analyzed in the time domain.

General Overview of the Software for Processing the Digitized ECG Signal

Figure 1:
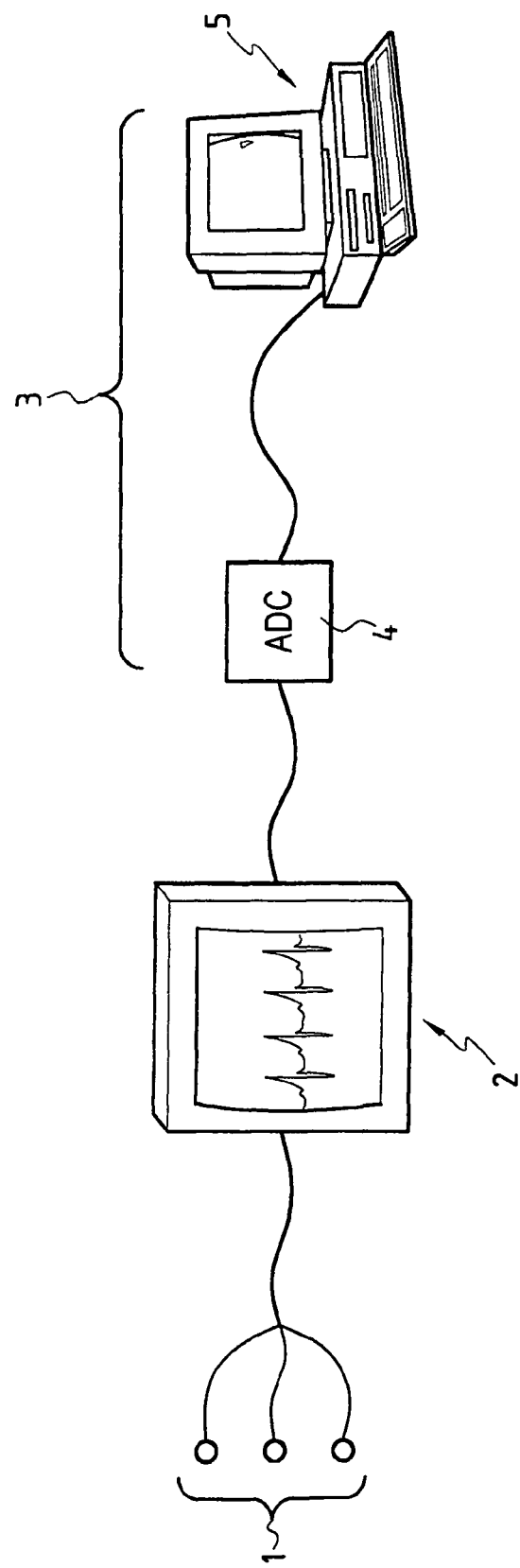
FIG. 1 is a diagram showing the main elements of a system in accordance with the invention for acquiring and frequency processing an ECG signal.
Figure 2:
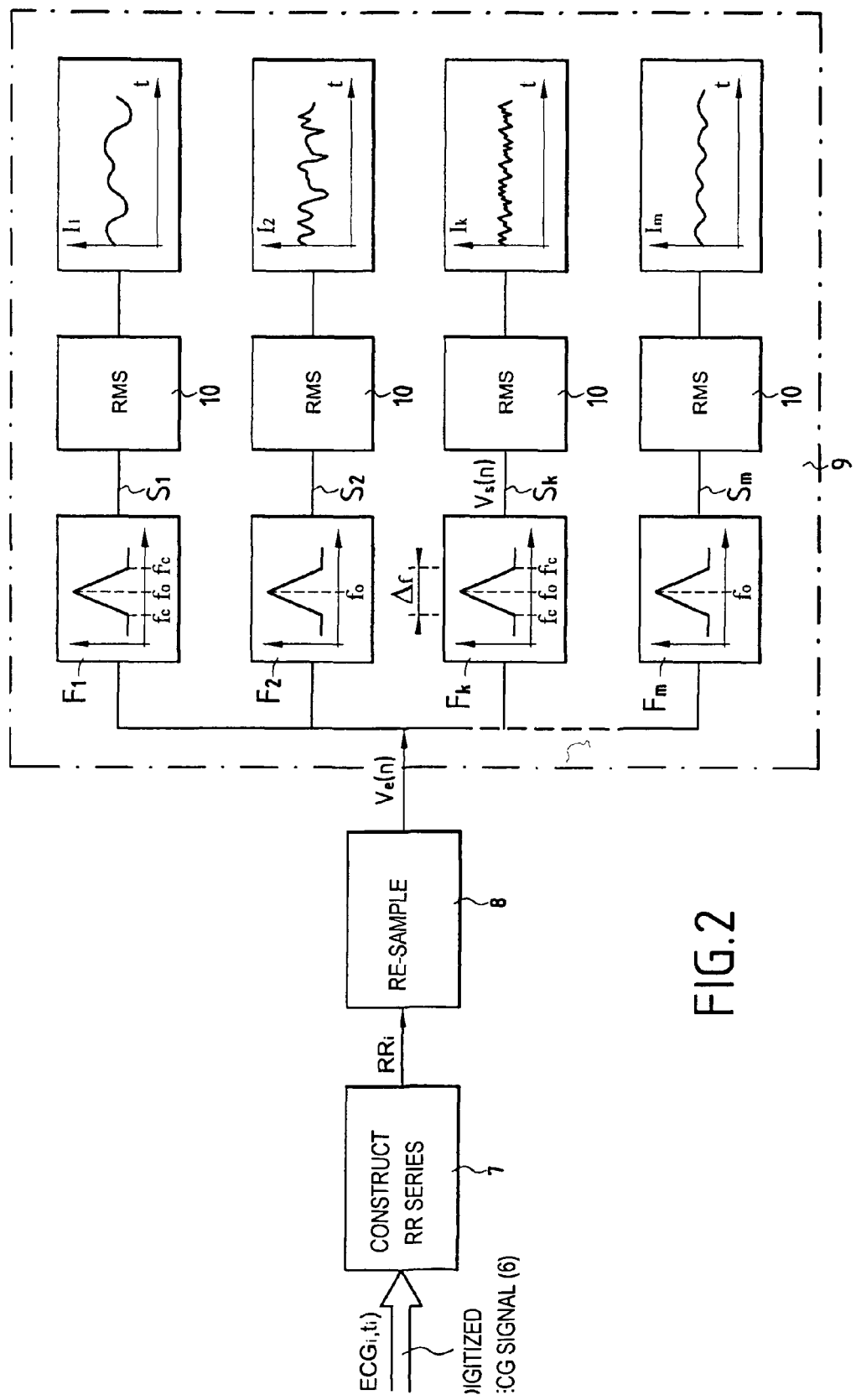
FIG. 2 is a block diagram showing the three main functional modules of the processing software executed by the processor unit of the FIG. 1 acquisition system.

FIG. 2 is a diagram showing the three main functional modules 7, 8, and 9 of the software for processing the digitized ECG signal.

The first module 7 receives at its input and in real time the successive digital data constituting the digitized ECG signal 6 as delivered by the analog-to-digital converter 4. For each sample that results from digitally converting the analog ECG signal, the data comprises the instantaneous amplitude $ECG_i$ of the ECG signal, together with the sampling instant $t_i$ ($t_i=n_i/f$, where $n_i$ is the sample number and f represents the sampling frequency of the converter 4).

The first module 7 is designed to detect automatically each successive peak $R_i$ in the digital signal 6, and to construct automatically an RR series from said signal. At its output, this module 7 delivers successively in time the successive points $RR_j$ of the series RR. The value of each point $RR_i$ is equal to the time interval $\delta t_i$ (expressed as a multiple of the sampling frequency f) between a peak $R_i$ and the following peak $R_{i+1}$ (in another variant that could be the preceding peak $R_{i-1}$).

The function of the second module 8 is to re-sample the RR series coming from the module 7 at a predefined frequency (e.g. 4 Hz, corresponding to a sampling period Ts of 250 milliseconds (ms)), in order to obtain at its output an RR series of samples $RR_i$ that are uniformly spaced apart in time, i.e. in other words, an RR series having sampling instants that are regular. This module 8 (which is known per se) performs this re-sampling by linear interpolation.

Given that the module 7 implementing the above-described function of detecting the peaks $R_i$ and constructing the RR series, and that the module 8 for re-sampling the RR series are already known, and implemented in particular in prior art solutions for performing spectral analysis based on computing the discrete Fourier transform, these two modules 7 and 8 are not described in greater detail herein.

The third module 9 is a module for frequency processing the re-sampled RR series, by implementing the frequency processing method of the invention.

The module 9 comprises m digital bandpass filters $F_1$ to $F_m$ in parallel, each filter being characterized by a predefined bandwidth [fc, f'c] which is specific thereto (where fc and f'c are the cutoff frequencies of the filter). At the output from each filter $F_1$ to $F_m$, a filtered discrete signal $S_1$ to $S_m$ is obtained made up solely of frequency components lying in the bandwidth of the filter.

In the context of the invention, any known type of digital bandpass filter may be used. For example, it is possible to use a digital bandpass filter made up of a highpass filter (cutoff frequency fc) and a lowpass filter (cutoff frequency f'c) connected in series.

In a preferred variant implementation, each filter ($F_1$ to $F_m$) is a recursive selective filter having an infinite impulse response (IIR) presenting a narrow bandwidth of width $\Delta f$ centered on a filter center frequency $f_0$.

More particularly, but in non-limiting manner, in a particular implementation, the transfer function $H(\omega)$ of each filter is defined by the following equation:

$$H(w) = \frac{1}{1 + j \cdot Q \cdot \left(\frac{w}{w_0} - \frac{w_0}{w}\right)}$$

in which:
  $\omega = 2\pi f$, where f is the frequency of the signal;

$\omega_0=2\pi f_0$, where $f_0$ represents the center frequency of the bandwidth; and $$Q = \frac{f_0}{\Delta f},$$

where $\Delta f$ represents the −3 decibel (dB) bandwidth of the bandwidth of the filter.

By applying the bilinear transform to $H(\omega)$, the following recurrence equation is obtained for the digital filter giving, for each sampling period n, the output sample vs(n) as a function of the input samples ve(n) and ve(n−2) and as a function of the output samples vs(n−1) and vs(n−2):

vs(n)=A.ve(n)+B.ve(n−2)+C.vs(n−1)+D.vs(n−2)

where:

$$A = \frac{1}{d_0};$$

$$B = -A;$$

$$C = \frac{\frac{4 \cdot Q}{w_0 \cdot Ts} - w_0 \cdot Q \cdot Ts}{d_0};$$

$$D = \frac{1 - \frac{2 \cdot Q}{w_0 \cdot Ts} - \frac{w_0 \cdot Q \cdot Ts}{2}}{d_0};$$

$$d_0 = 1 + \frac{2 \cdot Q}{w_0 Ts} + \frac{w_0 \cdot Q \cdot Ts}{2};$$

where Ts represents the period at which the RR series is re-sampled.

Each discrete filtered signal $S_1$ to $S_m$ is then processed by a digital module 10 which is designed to compute a variability index $I_1$ to $I_m$.

In the particular example shown in FIG. 2, and given by way of preferred implementation, each variability index $I_1$ to $I_m$ corresponds to the effective value of the corresponding discrete filtered signal $S_1$ to $S_m$. To compute the effective value, each module 10 is programmed with the rms algorithm, for example, in order to compute for each discrete filter signal $S_k$ a variability index $I_k$ in application of the following formula which is computed over a sliding computation window of period $T_0$:

$$I_k = \sqrt{\frac{1}{N} \sum_{i=1}^{N} Vs^2(i)}$$

where:

N represents the number of samples over a period $$T_0 = \frac{1}{f_0};$$

and

Vs(i) is the digital value of each sample output by the filter, i.e. the signal $S_k$.

It can be shown that the variability index $I_k$ as computed on the basis of the above-mentioned rms algorithm from a signal $S_k$ coming from a bandpass filter $F_k$ is substantially equal to the variability index that is usually computed in prior art solutions, which solutions are based on computing the spectral density curve by the fast Fourier transform, and then computing spectral power (i.e. the area under the spectral density curve) over the frequency range [fc, f'c].

The solution of the invention can thus advantageously replace prior art solutions for studying and/or monitoring cardiac rhythm, and it presents the advantage of being finer and of providing a better response time (eliminating the memory effect that is inherent to methods based on computing the Fourier transform or an equivalent). The solution of the invention is also simpler to implement and faster in computation time. The digital filtering algorithms and the algorithms for computing the variability indices as used in the method of the invention can firstly be designed more easily to operate in real time, and can secondly be implemented easily in a system of small size for monitoring cardiac rhythm, and in particular in a system of the outpatient type.

Particular examples of different IIR recursive selective filters $F_k$ are described below as preferred implementation variants, with these filters being particularly advantageous for studying cardiac rhythm. filter $F_1$: fc=0.04 Hz; f'c=0.15 Hz; $f_0$=0.095 Hz; $\Delta f$=0.11 Hz filter $F_2$: fc=0.15 Hz; f'c=0.5 Hz; $f_0$=0.325 Hz; $\Delta f$=0.35 Hz filter $F_3$: fc=0.04 Hz; f'c=0.15 Hz; $f_0$=0.27 Hz; $\Delta f$=0.46 Hz The variability index $I_1$ computed on the basis of the above-described rms algorithm, from the signal delivered by the particular above-described filter $F_1$ is a quantitative parameter which, for an adult, serves to characterize changes over time in sympathetic and parasympathetic tone.

The variability index $I_2$ computed on the basis of the above-described rms algorithm from the signal delivered by the particular above-mentioned filter $F_2$ is a quantitative parameter that serves, for an adult, to characterize changes over time in parasympathetic tone.

The variability index $I_3$ computed on the basis of the above-described rms algorithm from the signals coming from the above-described particular filter $F_3$ is a quantitative parameter giving an indication concerning variation over time between two successive heart beats (beat-to-beat variation).

Although in the context of the invention computing a variability index $I_k$ based on computing the effective value gives results that are particularly advantageous from the point of view of quantizing cardiac activity, it should nevertheless be emphasized that the invention is not limited to computing a variability index $I_k$ based on the effective value of each discrete filtered signal, but extends to any computation of a variability index $I_k$ that is a function of the instantaneous amplitude vs(n) of the corresponding discrete filtered signal $S_k$. Similarly, other frequency ranges for the bandwidth of a filter may be advantageous, and the invention is not limited to the particular frequency ranges given above.

Figure 6:
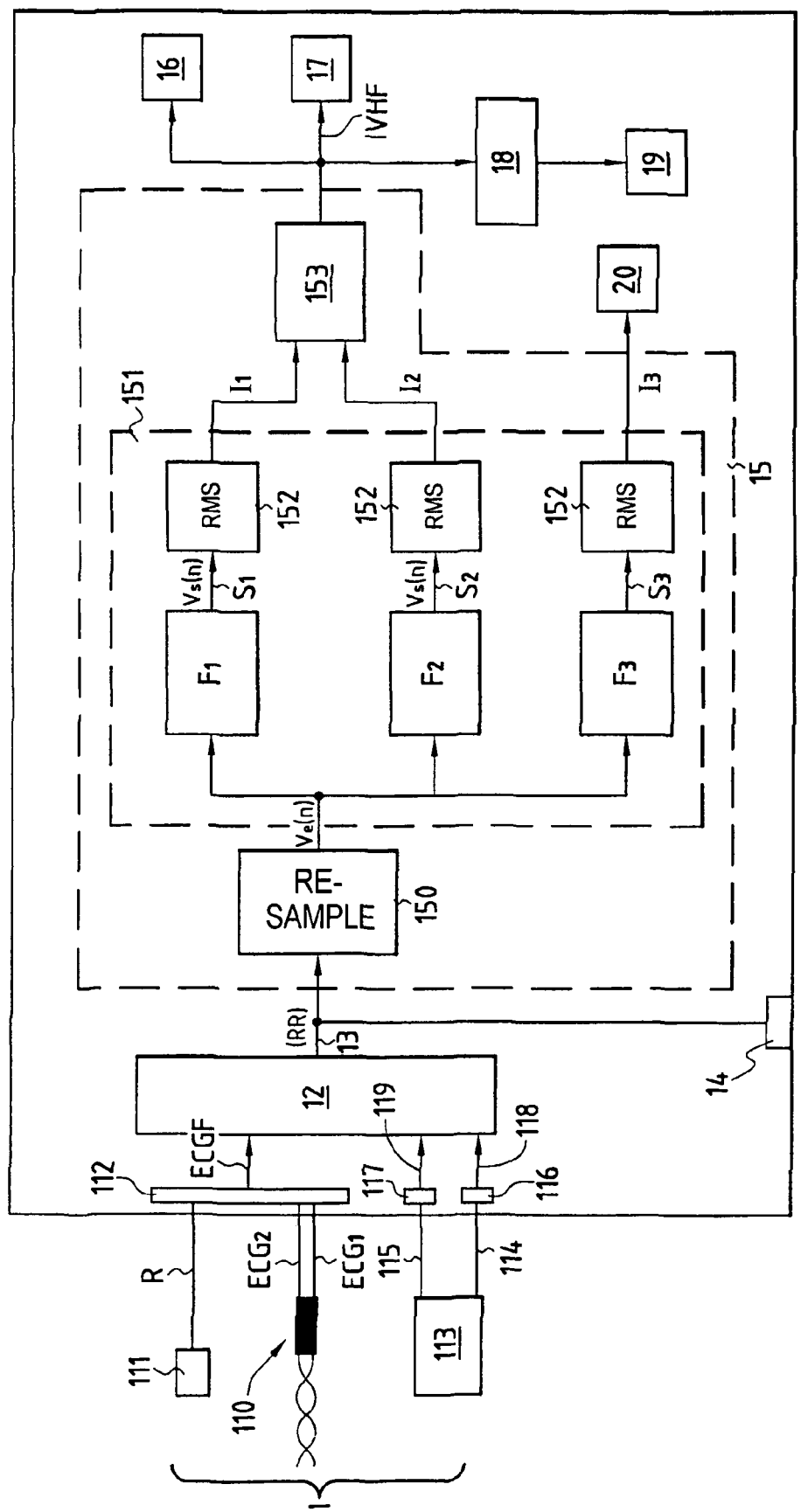
FIG. 6 is a block diagram of a cardiotocograph that has been improved so as to perform an additional function of real time monitoring of fetal suffering.

FIG. 6 shows another application of the invention to the field of monitoring fetal suffering. In this FIG. 6, there can be seen a block diagram of a cardiotocograph that makes it possible in the usual manner to measure the cardiac signal of a fetus, and which has been improved in a novel manner of the invention so as to perform an additional function of monitoring fetal suffering in real time.

In conventional manner, the cardiotocograph comprises:
means 11 for acquiring a fetal cardiac signal; and
a processor unit 12 (e.g. in form the of a microprocessor or a microcontroller) that receives as input the measurement signals delivered by the acquisition means 11, and that processes said measurement signals in conventional manner to deliver as outputs a digital type signal 13 forming an RR series.

The means 11 for acquiring the fetal cardiac signal are conventional and comprise:
- a two-turn electrode 110 which, in operation, is attached via the vagina to the scalp of the fetus, and delivers two analog measurement signals ECG1 and ECG2;
- a reference electrode 111 which, in operation, is placed in contact with the mother's thigh, and delivers a measurement signal R representative of maternal heart beat and serving as a reference signal; and
- electronic processor means 112 which output on the basis of the above-mentioned signals ECG1, ECG2, and R, a digital signal ECGF representative of the digitized fetal ECG signal.

The acquisition means 11 further comprise:
- an abdominal strap 113 which, in operation, is placed on the mother's abdomen and contains two sensors: an ultrasound sensor for ultrasound measurement of the fetal cardiac rhythm (analog measurement signal 114), and a pressure sensor for measuring contractions of the uterus (analog measurement signal 115); and
- conventional electronic circuits 116 and 117 for processing (in particular amplifying and sampling) the above-mentioned analog signals 114 and 115, and delivering respective digitized measurement signals 118 and 119.

The processor unit 12 of the cardiotocograph is programmed in particular to construct either on the basis of the digitized fetal ECG signal ECGF, or on the basis of the measurement signal 118, an RR series (digital signal 13) which is constituted by a succession of samples $RR_i$ defining respective time intervals between two successive fetal heart beats. The signal 13, i.e. the RR series, is made available in conventional manner on an output port 14 (a serial port or a parallel port) of the cardiotocograph.

The cardiotocograph of FIG. 6 is novel in that it includes an additional functional module 15 which performs real time processing of the RR series signal 13 delivered by the processor unit 12.

The module 15 comprises a first sub-module 150 for resampling the RR series, which sub-module is identical to the above-described module 8 of the variant shown in FIG. 2, and a second sub-module 151 for frequency processing the RR series, which sub-module is comparable with the above-described module 9 for the variant of FIG. 2.

More particularly, this second sub-module 151 comprises three IIR recursive selective digital filters $F_1$, $F_2$, and $F_3$ in parallel.

In a first variant embodiment:
filter $F_1$: fc=0.04 Hz; f'c=0.15 Hz; $f_0$=0.095 Hz; $\Delta f$=0.11 Hz
filter $F_2$: fc=0.15 Hz; f'c=0.5 Hz; $f_0$=0.325 Hz; $\Delta f$=0.35 Hz
filter $F_3$: fc=0.05 Hz; f'c=0.066 Hz; $f_0$=0.058 Hz; $\Delta f$=0.116 Hz In a second variant embodiment:
filter $F_1$: fc=0.031 Hz; f'c=0.102 Hz; $f_0$=0.0665 Hz; $\Delta f$=0.071 Hz
filter $F_2$: fc=0.102 Hz; f'c=0.5 Hz; $f_0$=0.301 Hz; $\Delta f$=0.398 Hz
filter $F_3$: fc=0.05 Hz; f'c=0.066 Hz; $f_0$=0.058 Hz; $\Delta f$=0.116 Hz The three discrete signals $S_1$, $S_2$, and $S_3$ coming from the filters $F_1$, $F_2$, and $F_3$ are processed in parallel by three modules 152 for computing the effective values of these signals (using the rms algorithm above described for the variant of FIG. 2).

Finally, the module 15 includes a module 153 for computing on the basis of the variability indices $I_1$ and $I_2$ computed in parallel by the modules 152, a high frequency variability index (HFVI) characteristic of fetal suffering.

The HFVI is preferably computed on the basis of one or other of following equations (1) and (2):

$$HFVI = \frac{I_2}{I_1} \quad (1)$$

$$HFVI = \frac{I_2}{I_1 + I_2} \quad (2)$$

With reference to FIG. 6, the index HFVI is provided in real time to a user of the cardiotocograph, non-exhaustively in two different ways:
- the instantaneous value of HFVI is displayed on the front of the cardiotocograph using a conventional display 16; and
- changes over time in HFVI are printed in the form of a time curve on a strip of paper, using a printer 17.

The index HFVI serves to quantify fetal suffering; below a predetermined threshold, it can be shown that the fetus is in a stage of fetal suffering. Thus, the practitioner using the cardiotocograph is informed in real time of the value of the index HFVI, and consequently of the level of fetal suffering.

Also in the variant embodiment of FIG. 6, the cardiotocograph has means 18 for detecting the index HFVI as delivered by the computation means 153, which detector means are designed to compare the instantaneous value of the index HFVI with at least one predetermined threshold, which threshold is preferably adjustable by the user of the cardiotocograph. When the value of the index HFVI is less than the predetermined threshold, the detector means 18 operate alarm means which may be of the visual and/or audible type, thereby alerting the practitioner.

In parallel with computing and processing the index HFVI as described above, the variability index $I_3$ derived from the signal $S_3$ coming from above-described filter $F_3$ constitutes a quantitative parameter that also enables fetal suffering to be characterized. Nevertheless, this parameter is less precise than the above-mentioned index FHVI. The instantaneous value of this index $I_3$ is displayed for the practitioner on a conventional display 20.

The module 15 for computing the indices FHVI and $I_3$ from the RR series can be an additional electronic module that is connected to the electronic mother card of the processor unit 12; the electronic architecture of the module 15 can be based on the use of a microcontroller or a microprocessor. It may also be programmable circuit of the electrically programmable logic device (EPLD) or the field programmable gate array (FPGA) type, or indeed it may be an application specific integrated circuit (ASIC) specially developed to perform the above-described functions of the module 15. Similarly, the functions of the module 15 could be performed by the processor unit 12, with the operation of said processor unit 12 being modified, for example, by adding a memory enabling it to perform the new functions of the module 15. Finally, in another variant embodiment, the module 15 could be a peripheral that is external to the cardiotocograph, and that is connected to the processor unit 12 of said cardiotocograph by the communications port 14.

The invention claimed is:

1. A method of frequency processing an RR series comprising filtering the RR series with at least one digital band-pass filter ($F_k$) presenting a predefined bandwidth [$f_c$, f'c] lying in the frequency range 0.04-2 Hz so as to obtain a discrete signal ($S_k$), and computing with a digital computing module, directly in the time-domain and over a time window lying in the range 0-25 s, a variability index ($I_k$) that is a function of the instantaneous amplitude [vs(n)] of the discrete signal ($S_k$) from said band-pass filter.

2. A method according to claim 1, wherein said at least one digital band-pass filter is an infinite impulse response recursive selective filter.

3. A method according to claim 1, wherein the variability index ($I_k$) is equal to discrete signal ($S_k$) RMS value from the band-pass filter.

4. A method according to claim 1, wherein the bandwidth of the at least one digital filter lies in one of the frequency bands:
0.04-0.5 Hz
[0.04 Hz, 0.5 Hz].

5. A method according to claim 1, comprising acquiring and electronically processing an analog cardiac signal characteristic of cardiac rhythm, comprising recording and digitizing said cardiac signal, and constructing an RR series, further comprising automatic and real time processing of said RR series as said series is constructed.

6. A process according to claim 5, wherein the analog cardiac signal is a fetal cardiac signal.

7. A method of frequency processing an RR series comprising filtering the RR series with a plurality of filters ($F_1, F_2, \ldots$) each presenting a predefined bandwidth [fc, f'c] lying in the frequency range 0.04-2 Hz, so as to obtain a plurality of discrete signals ($S_k$), and computing with a digital computing module, directly in the time-domain and over a time window lying in the range 0-25 s, in parallel, a plurality of variability indices ($I_1, I_2, \ldots$) that are respectively a function of the instantaneous amplitude [vs(n)] of said discrete signals ($S_k$) from said band-pass filters ($F_1, F_2, \ldots$), and a frequency variability index that is a function of said plurality of variability indices ($I_1, I_2, \ldots$).

8. A method according to claim 7, wherein the plurality of filters ($F_1, F_2, \ldots$) comprises at least one first filter ($F_1$) of bandwidth lying in the frequency band 0.04-0.15 and one second filter ($F_2$) of bandwidth lying in the frequency band 0.15-2 Hz.

9. A method according to claim 7, wherein the bandwidth of the second filter ($F_2$) lies in the frequency band 0.15-0.5 Hz.

10. A system for acquiring and processing in real time a cardiac signal, which system comprises acquisition means for acquiring said cardiac signal, first electronic means for automatically constructing an RR series, said series being made up of a plurality of samples ($RR_1$) respectively defining time intervals between successive pairs of heart beats from said cardiac signal, the system further comprising second electronic means for processing the RR series delivered by the first electronic means comprising means for filtering the RR series with at least one digital band-pass filter ($F_k$) presenting a predefined bandwidth [fc, f'c] lying in the frequency range 0.04-2 Hz so as to obtain a discrete signal ($S_k$), and means for computing, directly in the time-domain and over a time window lying in the range 0-25 s, a variability index ($I_k$) that is a function of the instantaneous amplitude [vs(n)] of the discrete signal ($S_k$) from said band-pass filter.

11. A system for acquiring and processing in real time the cardiac signal of a fetus, which system comprises means for acquiring the cardiac signal of a fetus, first electronic means for automatically constructing an RR series, said series being made up of a plurality of samples ($RR_1$) respectively defining time intervals between successive pairs of heart beats, the system further comprising second electronic means for processing the RR series delivered by the first electronic means comprising means for filtering the RR series with at least one digital band-pass filter ($F_k$) presenting a predefined bandwidth [fc, f'c] so as to obtain a discrete signal ($S_k$), and means for computing, directly in the time-domain and over a time window lying in the range 0 -25 s, a variability index ($I_k$) that is a function of the instantaneous amplitude [vs(n)] of the said discrete signal ($S_k$) from said band-pass filter, said means for filtering the RR series comprising at least two filters ($F_1, F_2$) of bandwidth lying respectively in the following frequency bands:
$F_1$: 0.04-0.15 Hz;
$F_2$: 0.15-2 Hz;
and for computing a frequency variability index as a function of the variability indices $I_1$ and $I_2$.

12. A cardiotocograph comprising a system according to claim 11, further comprising means for measuring fetal suffering on the basis of the frequency variability index.

* * * * *